United States Patent [19]

Dougherty

[11] Patent Number: 5,171,741
[45] Date of Patent: Dec. 15, 1992

[54] BACTERIOCHLOROPHYLL-A DERIVATIVES USEFUL IN PHOTODYNAMIC THERAPY

[75] Inventor: Thomas J. Dougherty, Grand Island, N.Y.

[73] Assignee: Health Research, Inc., Buffalo, N.Y.

[21] Appl. No.: 341,591

[22] Filed: Apr. 21, 1989

[51] Int. Cl.$^5$ ............................................. A61K 31/40
[52] U.S. Cl. ................................ 514/185; 204/157.61; 514/410; 540/145
[58] Field of Search ................. 540/145; 514/185, 410

[56]  References Cited

U.S. PATENT DOCUMENTS

| 4,649,151 | 3/1987 | Dougherty et al. | 514/410 |
| 4,727,027 | 2/1988 | Weisehahn et al. | 435/173 |
| 4,752,958 | 6/1988 | Weinstein et al. | 514/410 |

FOREIGN PATENT DOCUMENTS

| 220686 | 6/1987 | European Pat. Off. |
| 60-000981 | 1/1985 | Japan . |
| 63-4805 | 1/1988 | Japan . |

OTHER PUBLICATIONS

Lipson et al., *J. Natl. Cancer Inst.* (1961) 26:1-11.
Dougherty et al., *Cancer Res.* (1978) 38:2628-2635.
Dougherty et al., *J. Nat. Cancer Inst.* (1979) 62(2):231-237.
Dougherty et al., "Cancer: Principles and Practice of Oncology" (1982) de Vita, Jr., et al., editors, pp. 1836-1844.
Mew et al., *J. Immunol.* (1983) 130:1473-1477.
Weishaupt et al., *Cancer Res.* (1976) 36:2326-2329.
Matthews et al., *Transfusion* (1988) 28(1):81-83.
Beems et al., *Photochemistry and Photobiology* (1987) 46(5):639-643.

*Primary Examiner*—Richard L. Raymond
*Attorney, Agent, or Firm*—Irell & Manella

[57]  ABSTRACT

Compounds of fomula (1) or formula (2):

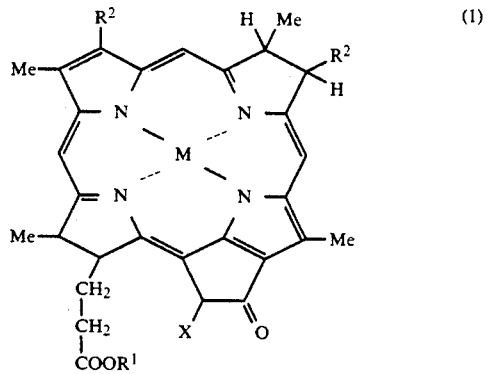

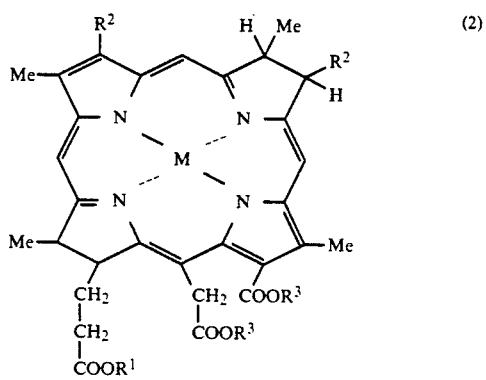

wherein M is a non-paramagnetic metal selected from $Mg^{+2}$, and $Zn^{+2}$, or represents $2 H^+$ each $H^+$ bonded to one of the N atoms connected by the solid lines;
$R^1$ is a saturated or unsaturated hydrocarbyl residue of 8-25C;
each $R^2$ is independently selected from the group consisting of vinyl, ethyl, acetyl and 1-hydroxyethyl, and X is $COOR^3$, wherein $R^3$ is alkyl (1-4C);
are useful in photodynamic therapy and diagnosis. These compounds photosensitize target biological substrates to irradiation, and treating said substrates with these sensitizers followed by irradiation leads to the impairment or destruction of the biological substrate. When administered systemically, these compounds accumulate in the undesired target biological substrate. The compounds can also be utilized in vitro, for example to destroy infectious cells or viruses in blood intended for transfusion.

10 Claims, 4 Drawing Sheets

FIG.I-I

TUMOR RESPONSE IN THE SMT-F TUMOR (DBA/2 Ha MICE)

| DRUG DOSE (mg/kg, i.v.) | TIME INTERVAL (h) | WAVELENGTH (nm) |
|---|---|---|
| 3.0 | 2 | 680 |
| " | 2 | 750 |
| " | 2 | 780 |
| 5.0 | 2 | 780 |
| " | 2 | 630 |
| " | 2 | 670 |
| " | 2 | 726 |
| " | 2 | 740 |
| " | 2 | 760 |
| " | 2 | 790 |
| " | 2 | 800 |
| 10.0 | 24 | 630 |
| " | 24 | 680 |
| " | 24 | 750 |
| " | 24 | 780 |
| " | 24 | 799 |
| 5.0 | 1 | 780 |
| 10 | 1 | 780 |
| 10 | 2 | 780 |
| 20 | 2 | 780 |
| 10 | 24 | 780 |
| 20 | 24 | 780 |
| 30 | 24 | 780 |
| 10 | 2 | 780 |
| 10 | 24 | 780 |
| 20 | 24 | 780 |
| 20 | 48 | 780 |
| 20 | 72 | 780 |
| 20 | 96 | 780 |
| 20 | 120 | 780 |
| 20 | 1 | 780 |
| 20 | 2 | 780 |

FIG.1-2

| LIGHT DOSE (j/cm²) | TUMOR RESPONSE DAY 7 | DAY 30+ | |
|---|---|---|---|
| 270 | 3/5 | 0 | |
| 270 | 3/6 | 0 | |
| 270 | 3/6 | 0 | |
| 270 | 18/26 (69%) | 4/26 (15%) | |
| 270 | 2/6 | 0 | |
| 270 | 6/6 | 0 | |
| 270 | 5/5 | 0 | |
| 270 | 3/3 | 0 | |
| 270 | 4/4 | 3/4 | |
| 270 | 3/6 | 1/6 | |
| 270 | 2/5 | 0 | |
| 270 | 0/5 | 0 | |
| 270 | 5/5 | 0 | |
| 270 | 9/10 | 0 | |
| 270 | 9/12 | 0 | |
| 270 | 0 | 0 | |
| 540 | 3/5 | 0 | |
| 540 | 5/5 | 4/5 | |
| 540 | 4/4 | 0 | |
| 540 | 5/5 | 1/5 | |
| 540 | 4/30 | 0 | UNCERTAIN DOSIMETRY |
| 540 | 4/9 | 0 | |
| 540 | 4/5 | 0 | |
| 1080 | 2/5 | 1/5 | |
| 1080 | 10/13 | 0 | |
| 1080 | 4/5 | 1/5 | |
| 1080 | 5/5 | 0 | |
| 1080 | 0/7 | 0 | |
| 1080 | 2/5 | 0 | |
| 1080 | 0/5 | 0 | |
| 1080 | 3/3 | 1/3 | |
| 1080 | 4/4 | 2/4 | |

BACTERIOCHLOROPHYLL-A DERIVATIVES USEFUL IN PHOTODYNAMIC THERAPY

TECHNICAL FIELD

The invention relates to the field of photodynamic therapy and related treatment of in vitro samples using light-absorbing resonant ring systems and irradiation. More specifically, the invention is directed to methods of in vivo photodynamic therapy and diagnosis and in vitro sterilization using bacteriochlorophyll-a and its related compounds.

BACKGROUND ART

Photodynamic therapy using porphyrins and related compounds has, by now, a fairly long history. Early work, in the 1940s, demonstrated that porphyrin could be caused to fluoresce in irradiated tumor tissue. The porphyrins appeared to accumulate in these tissues, and were capable of absorbing light in situ, providing a means to detect the tumor by the location of the fluorescence. A widely used preparation in the early stages of photodynamic treatment both for detection and for therapy was a crude derivative of hematoporphyrin, also called hematoporphyrin derivative, HpD, or Lipson derivative prepared as described by Lipson and coworkers in *J Natl Cancer Inst* (1961) 26:1–8. Considerable work has been done using this preparation, and Dougherty and coworkers reported the use of this derivative in treatment of malignancy (*Cancer Res* (1978) 38:2628–2635; *J Natl Cancer Inst* (1979) 62:231–237).

Dougherty and coworkers prepared a more effective form of the hematoporphyrin derivative which comprises a portion of HpD having an aggregate weight >10 kd. This form of the drug useful in photodynamic therapy is the subject of U.S. Pat. No. 4,649,151, is commercially available, and is in clinical trials.

The general principles of the use of light-absorbing compounds, especially those related to porphyrins, has been well established as a treatment for tumors when administered systemically. The differential ability of these preparations to destroy tumor, as opposed to normal tissue, is due to the homing effect of these preparations to the objectionable cells. (See, for example, Dougherty, T. J., et al., "Cancer: Principles and Practice of Oncology" (1982), V. T. de Vita, Jr., et al., eds., pp. 1836–1844.) Efforts have been made to improve the homing ability by conjugating hematoporphyrin derivative to antibodies. (See, for example, Mew, D., et al., *J Immunol* (1983) 130:1473–1477.) The mechanism of these drugs in killing cells seems to involve the formation of singlet oxygen upon irradiation (Weishaupt, K. R., et al., *Cancer Research* (1976) pp. 2326–2329).

The use of hematoporphyrin derivative or its active components in the treatment of skin diseases using topical administration has also been described in U.S. Pat. No. 4,753,958. In addition, the drugs have been used to sterilize biological samples containing infectious organisms such as bacteria and virus (Matthews, J. L., et al., *Transfusion* (1988) 28:81–83). Various other photosensitizing compounds have also been used for this purpose, as set forth, for example, in U.S. Pat. No. 4,727,027.

In general, the methods to use radiation sensitizers of a variety of structures to selectively impair the functioning of biological substrates both in vivo and in vitro are understood in the art. The compounds useful in these procedures must have a differential affinity for the target biological substrate to be impaired or destroyed and must be capable of absorbing light so that the irradiated drug becomes activated in a manner so as to have a deleterious effect on the adjacent compositions and materials.

Because it is always desirable to optimize the performance of therapeutics and diagnostics, variations on the porphyrin drugs traditionally used in treatment and diagnosis have been sought. A number of general classes of photosensitizers have been suggested including phthalocyanines, psoralen-related compounds, and multicyclic compounds with resonant systems in general. Most similar to the compounds disclosed herein are various pheophorbide derivatives whose use in photodynamic therapy has been described in EPO Application 220686 to Nihon Metaphysics Company; ethylene diamine derivatives of pheophorbide for this purpose described in Japanese Application J85/000981 to Tama Seikayaku, K. K., and Japanese Application J88/004805 which is directed to 10-hydroxy pheophorbide-a. In addition, pheophorbide derivatized to a long chain hydrocarbyl group has been disclosed as useful in photodynamic therapy in U.S. Ser. No. 221,804, filed Jul. 20, 1988, assigned to the same assignee and incorporated herein by reference. In addition, Beems, E. M., et al., in *Photochemistry and Photobiology* (1987) 46:639–643 discloses the use as photosensitizers of two derivatives of bacteriochlorophyll-a —bacteriochloro-phyllin-a in which the exocyclic ring is opened and lacks the phytyl alcohol derivatized in bacteriochlorophyll-a) and bacteriochlorin-a (which is similar to bacteriochlorophyllin but lacks the Mg ion. These authors direct their attention to these derivatives as being advantageous on the grounds of enhanced water solubility as compared to bacteriochloro-phyll-a.

The problem remains to find suitable photosensitizers useful in photodynamic therapy and diagnosis which are optimal for particular targets and particular contexts. It is unlikely whether a single compound or small group of compounds, while generally applicable, would be of maximum benefit in every instance. Thus, the invention provides an additional group of photosensitizing compounds which becomes part of the repertoire of candidates for use in specific therapeutic and diagnostic situations.

DISCLOSURE OF THE INVENTION

The invention provides alternative methods of photodynamic therapy and diagnosis using a group of compounds related to the tetrahydroporphyrins, such as bacteriochlorophyll-a or -b or the corresponding bacteriochlorins. These compounds are of formula (1) or formula (2):

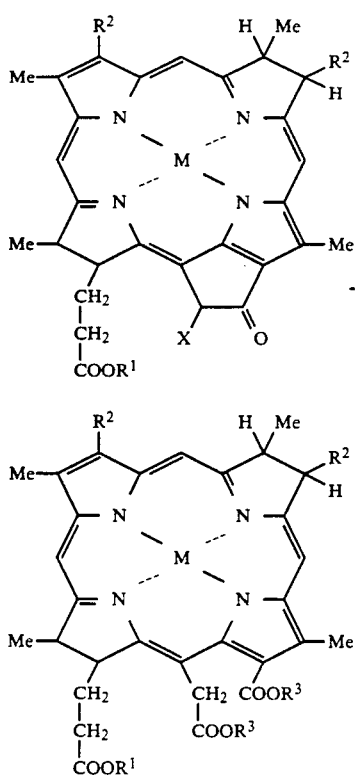

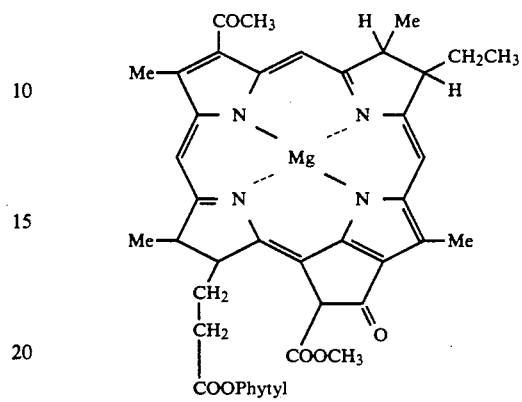

wherein

M is a non-paramagnetic metal selected from $Mg^{+2}$, $Sn^{+2}$, and $Zn^{+2}$, or represents 2 $H^+$, each $H^+$ bonded to one of the N atoms connected by the solid lines;

$R^1$ is a saturated or unsaturated hydrocarbyl residue of 8-25C;

each $R^2$ is independently selected from the group consisting of vinyl, ethyl, acetyl and 1-hydroxyethyl, and X is $COOR^3$, wherein $R^3$ is alkyl (1-4C).

Thus, in one aspect, the invention is directed to a method to effect the impairment or destruction of a target biological substrate which method comprises treating the target substrate with an amount of the compound of formula 1 effective to photosensitize said substrate followed by irradiating said target substrate with radiation in a wavelength band absorbed by the compound of formula 1 for a time effective to impair or destroy the substrate.

In other aspects, the invention is directed to pharmaceutical compositions useful in the foregoing method, and to diagnostic kits which include the compound of formula 1.

BRIEF DESCRIPTION OF THE DRAWINGS

FIGS. 1-1 and 1-2 are tables showing the results of treatment with bacteriochlorophyll-a at various total radiation energies, wavelengths and time intervals between injection of the sensitizer and light treatment.

FIG. 2 shows the action spectrum constructed from the table of FIG. 1.

MODES OF CARRYING OUT THE INVENTION

Figure 2:
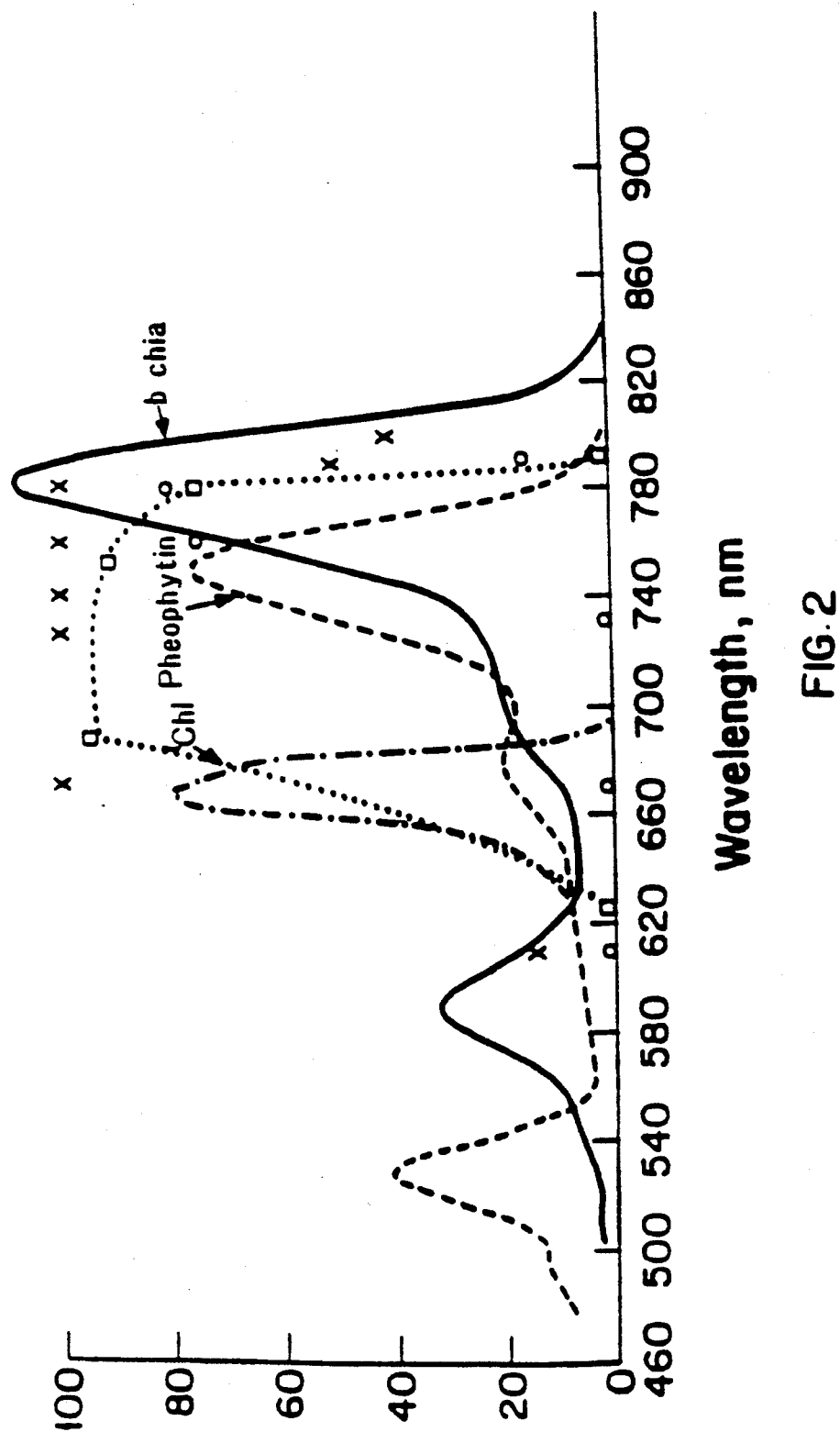

Bacteriochlorophyll-a (bchla) is a tetrahydroporphyrin found in certain photosynthetic bacteria, for example, Rhodopseudomonas virdis. Bchla has the formula:

Bchla is essentially identical to the chlorophyll-a of higher plants except that ring B is in the dihydro form and the vinyl group in ring A is converted to an acetyl group. The wavelength absorption maximum of bchla is about 780 nm and the extinction coefficient in this region is quite high ($E_{780}=75,000$). This long wavelength absorption is advantageous because light penetrates tissues 2-3 times more effectively at a wavelength near 800 nm versus lower wavelengths, e.g., 630 nm.

Bchla is readily obtained by extraction from bacterial sources, and is available commercially from Porphyrin Products, Logan, Utah. Although the material is readily oxidized, especially in the presence of light, and the magnesium ion is readily removed in the presence of dilute acid, bchla is sufficiently stable in vivo to be an effective phototherapeutic agent.

In bacteriochlorophyll-b, which can also readily be obtained from bacterial sources, $R^2$ in the B ring is vinyl rather than ethyl. The other embodiments of $R^2$ can easily be prepared starting with bacteriochlorophyll-b by standard hydration of the vinyl group to obtain the 1-hydroxyethyl substituent, and mild oxidation to obtain the corresponding acetyl substituent. Similarly, the $R^2$ substituent in ring A can be reduced to the 1-hydroxyethyl and/or dehydrated to vinyl and/or reduced to ethyl.

Conversion of the compounds of formula 1 to the compounds of formula 2 can readily be effected by opening of the cyclopentanone ring using known reagents, such as alkaline solution in the presence of oxygen as described in "Porphyrins and Metalloporphyrins", Smith, K., ed. (1975) Elsevier Press, pp. 52-53. Although the phytyl group is removed in this reaction, reesterification to the desired $R^1$ can be effected by standard methods.

In general, alternate embodiments of $R^1$ or $R^3$ in either formula 1 or formula 2 can be obtained by transesterification or by hydrolysis and reesterification. In some instances, this esterification should be conducted on the compounds when they are in the form of the corresponding porphyrin or dihydroporhryrins obtained by oxidation, for example, using osmium tetroxide and then re-reducing to the tetrahydro form. In all of the conversions set forth above, it may be necessary to conduct the reactions in a certain order, to restore or remove the metal substituent and/or to utilize protective reactions and groups as is understood by practitioners in the art.

The compounds of formulas 1 and 2 are used for photodynamic therapy and diagnosis with respect to target biological substrates. By "target biological substrate" is meant any cells, viruses or tissues which are undesirable in the environment to which therapy or other corrective action, such as sterilization, is employed, or the location of which is desired to be known in an environment to which diagnosis is applied. For example, in a manner analogous to the use of the active fraction of hematoporphyrin derivative (Hpd), as described in U.S. Pat. No. 4,649,151, incorporated herein by reference, neoplastic tissue is effectively treated in vivo by virtue of the ability of the drug to accumulate preferentially in such tissue, and by virtue of the photosensitizing nature of the drug. In this instance, the target biological substrate is the neoplastic tissue. As described in this patent, the drug is injected into the subject, and permitted to clear normal tissue. Then the neoplastic tissue is exposed to radiation at a wavelength appropriate to its absorption spectrum. The patent further describes the synergistic effect of heat supplied, if desired, by infrared irradiation. In addition, the location of the tumor can be ascertained by the fluorescence of the drug.

In another application, Matthews, J. L., et al., *Transfusion* (1988) 28:81-83, describe the use of the photosensitizing compounds HpD and the active fraction thereof, designated DHE, in eradicating pathogens from fluids in vitro. This article describes techniques for treating blood or other biological fluids to eliminate pathogens such as protozoa, virus, bacteria, fungi, and so forth. Similarly, U.S. Pat. No. 4,727,027 describes the use of furocoumarin in conjunction with irradiation by UV light for decontamination of blood products. In these instances, the target substrates are pathogens which may include a variety of "organisms" such as viruses and protozoa, as well as bacteria and fungi.

In U.S. Pat. No. 4,753,958, topical treatment of skin diseases using photosensitizing drugs is described. In this instance, the target biological substrate is the infectious virus or cell carrying the disease. This too, may be a virus, bacterium, or other microorganism, including fungal infections.

For use in the method of the invention, the compounds of formula 1 and 2 are formulated using conventional excipients appropriate for the intended use. For systemic administration, in general, buffered aqueous compositions are employed, with sufficient nontoxic detergent to solubilize the active compound. As the compounds of formulas 1 and 2 are generally not very soluble in water, a solubilizing amount of such detergent is employed. Suitable nontoxic detergents include Tween-80, various bile salts, such as sodium glycholate, various bile salt analogs such as the fusidates. Alternate compositions utilize liposome carriers. The solution is buffered at neutral pH using conventional buffers such as Hank's solution, Ringer's solution, or phosphate buffer. Other components which do not interfere with the activity of the drug may also be included, such as stabilizing amounts of proteins, for example, serum albumin.

Systemic formulations can be administered by injection, such as intravenous, intraperitoneal, intramuscular, or subcutaneous injection, or can be administered by transmembrane or transdermal techniques. Formulations appropriate for transdermal or transmembrane administration include sprays and suppositories containing penetrants, which can often be the detergents described above.

For topical local administration, the formulation may also contain a penetrant and is in the form of an ointment, salve, liniment, cream, or oil. Suitable formulations for both systemic and localized topical administration are found in *Remington's Pharmaceutical Sciences,* latest edition, Mack Publishing Co., Easton, Pa.

For use ex vivo to treat, for example, blood or plasma for transfusion or preparations of blood products such as Factor VIII, no special formulation is necessary, but the compounds of formula 1 and 2 are dissolved in a suitable compatible solvent and mixed into the biological fluid at a suitable concentration, typically of the order of 1-100 ug/ml prior to irradiation.

For photodynamic therapeutic and diagnostic applications, suitable dosage ranges will vary with the mode of application and the choice of the compound, as well as the nature of the condition being treated or diagnosed. However, in general, suitable dosages are of the order of 0.1-50 mg/kg body weight, preferably 1-3 mg/kg. For topical administration, typically amounts on the order of 50-100 mg total are employed.

The general procedures for photodynamic therapy and diagnosis in vivo are analogous to those described in U.S. Pat. No. 4,649,141; those for ex vivo treatment are analogous to those described by Matthews, J. L., et al., *Transfusion* (supra); topical methods are analogous to those described in U.S. Pat. No. 4,753,958; all are incorporated herein by reference.

Briefly, for systemic administration/ a suitable time period after administration, typically from several hours to two days is allowed to elapse in order to permit concentration of the drug of formula 1 or 2 in the target biological substrate. In general, this substrate will be a tumor, and the localization of the compound of formula 1 or 2 can be monitored by measuring the fluorescence or absorption of the target tissue as compared to background. After localization has been accomplished, the target biological substrate is irradiated with a suitable band of irradiation, in the case of the compounds of formula 1, in the range of 750-800 nm at a rate of 5 mW/cm$^2$-0.75 W/cm$^2$, and a total energy of 100-1000 J/cm$^2$.

For topical treatment, localization is immediate, and the corresponding radiation can be provided immediately. For treatment of biological fluids ex vivo, again, no localization interval is required, and radiation is applied on the order of 1-10 J/cm$^2$. Because penetration of tissue is not required, lower total energy can be employed.

The following example, directed to bchla, is intended to illustrate but not to limit the invention. The remaining compounds of formulas 1 and 2 have similar absorption spectra as they contain the same tetrahydroporphyrin resonance system, and have similar solubilities.

EXAMPLE 1

Formulation of bchla

Bacteriochlorophyll-a, obtained at >90% purity from Porphyrin Products (Logan, Utah) was dissolved at a concentration of 5 mg/ml in Tween-80 (Sigma) by stirring for several hours or overnight. The resulting solution was mixed with 9 volumes of Hank's buffer solution with agitation until all of the detergent solution was dissolved. Any remaining particulate matter is removed by filtration and the concentration of the final solution is determined spectrophotometrically using a 1:100 dilution in distilled water ($OD_{780}=87.3$ for 1 mg/ml of concentrate). In general, if the initial solution of bchla is conducted carefully, the resulting formulation has a concentration of bchla of 0.5 mg/ml.

EXAMPLE 2

Effect of bchla on Tumors

DBA2/HaD mice were transplanted with SMT-F tumors. When the subcutaneous tumors reached 4.5–5.5 mm in diameter, the mice, in groups of five, were injected intravenously with the bchla solution of Example 1 in doses of 5–30 mg/kg. At a time 1 hour-5 days later, the tumor, previously shaved and depiliated, plus a margin of 2–3 mm was exposed to radiation of a wavelength in the range 630–800 nm using a Spectraphysics argon dye laser with Exciton LDS751 dye, tunable over the 700–800 nm range or a diode laser—e. g., Spectra Diode emitting in the 750–850 nm range or a Xenon arc lamp filtered with an interference filter to pass 90% of the 700 nm light ±60 nm at dose rates of 75–150 $mW/cm^2$. When the Xenon system was used, mild hyperthermia resulted (42° C. at 160 $mW/cm^2$). It is not known whether this temperature rise acts synergistically with bchla as has been shown with HpD and its active fraction.

Tumor response is shown in the table of FIG. 1 for the seventh day after light treatment which indicates regression, and at a time point at least 30 days after light treatment, which would indicate cure, if there had been no regrowth.

As shown in FIG. 1 good response to bchla was obtained, for example, after 2 hours at 5 mg/kg in the 670–790 nm range and after 24 hours after injection with 10 mg/kg and irradiated at 680–780 nm.

FIG. 2 shows the action spectrum along with the absorption spectra of bchla, pheophytin (demetalated bchla, found in vivo) and for chlorophyll (oxidized bchla, theoretically found in vivo). The "X"s represent the 7 day response when 270 $J/cm^2$ were used 2 hours after the administration of 5 mg/kg; the squares represent the 7 day response when 270 $J/cm^2$ were administered 24 hours after administration of 10 mg/kg, and the circles represent the 30 day (cure) response, all as a function of wavelength of light used to treat the tumor.

EXAMPLE 3

Determination of Therapeutic Ratio

One of the undesirable side effects of photodynamic therapy using certain compounds is cutaneous photosensitivity unrelated to the target biological substrate. Accordingly, the effect of the treatment on the photosensitivity of the foot of the treated mice was measured. The response of the foot was measured as erythema and/or edema (or loss of skin or further damage).

Figure 3:
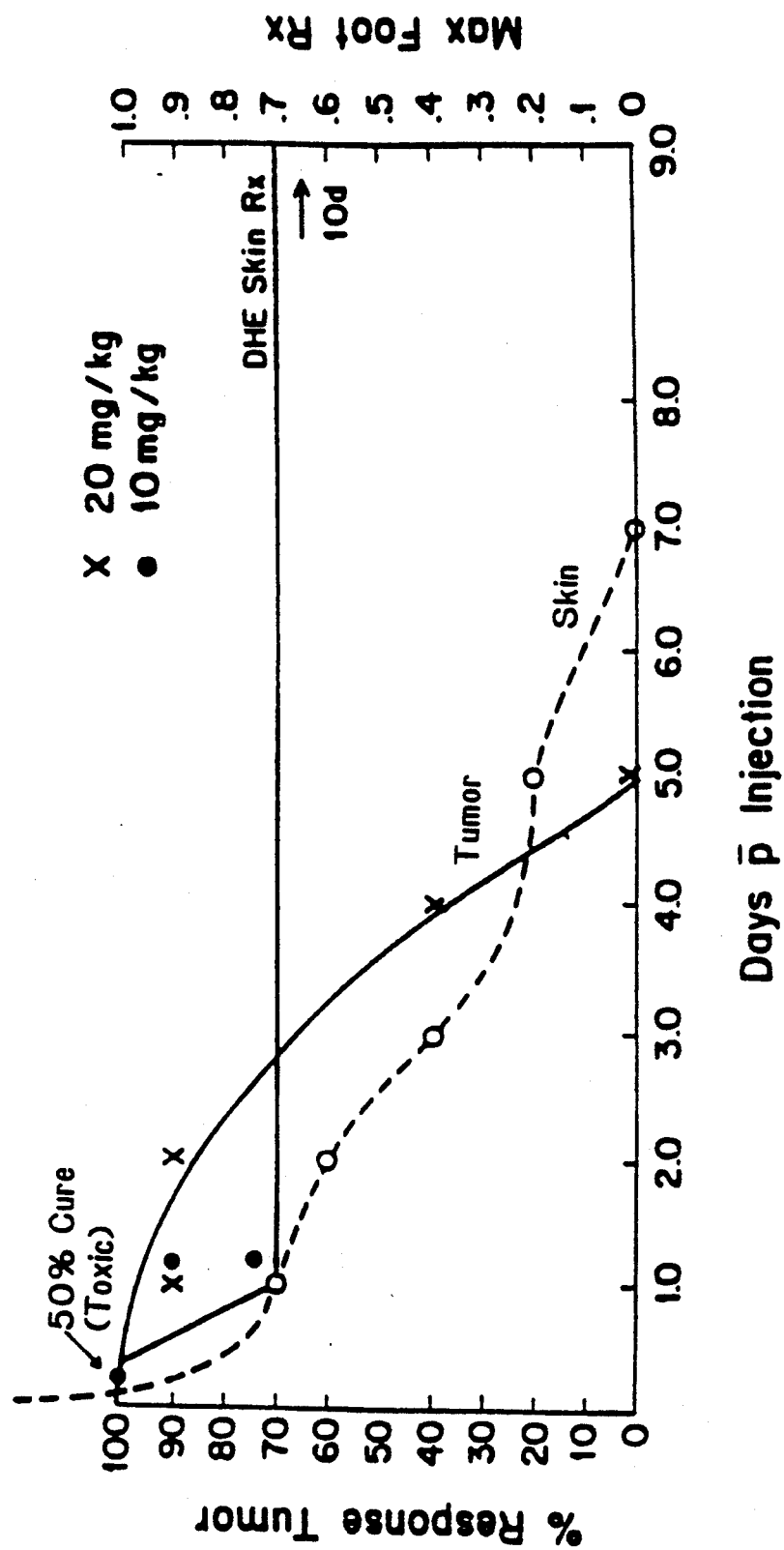
FIG. 3 shows the tumor response as compared to foot sensitization to bacteriochlorophyll-a as a function of time.

The results are shown in FIG. 3. The left ordinate shows the percentage of tumors which responded; the right ordinate is an arbitrary scale for the foot response wherein 1.0 represents severe erythema and edema; 0.1 represents little effect, and 0.5 represents a moderate reaction. The results show that for bchla, the sensitivity of the tumor and the skin of the foot declined concomitantly, while for the active component of hematoporphyrin derivative designated DHE, the sensitivity persists for more than 10 days after injection. Thus, with DHE the tissue (foot) would be sensitive to light (for example, sunlight) for an extended period of time (30 days in humans), whereas for bchla, sensitivity could be expected to persist for only a few days.

EXAMPLE 4

Metabolism of bchla

Uptake and clearance of bchla in tumor and liver were measured by extraction of the tumor or liver tissue with 1:1$MeOH:CH_2Cl_2$, followed by HPLC analysis. The levels of bchla in tumor and liver after injection of bchla are shown in Table 1.

TABLE 1

| bchla Uptake in DBA/2 Ha Mice in SMT-F Tumor | | |
|---|---|---|
| Dose bchla | Time After | Tissue Level (ug/g) |
| (mg/kg) | Injection | Tumor | Liver |
| 10 | 2 h | 6.14 | 44 |
| 10 | 24 h | — | 49.4* |
| 20 | 2 h | 16 | — |
| 20 | 24 h | 10–19.7* | — |
| 10 | 48 h | 10.7* | — |

*Values at time intervals of 1 day or more are uncertain since preliminary experiments indicate conversion to other components (see below).

These results show that both tumor and liver have high levels of the compound after 2 hours and that these levels are maintained for as long as 24 or 48 hours.

However, partial conversion to bacteriopheophytin occurs at 24 hours or more in tumor and 2 hours in liver. Two hours after injection, the tumor contains essentially only bchla with a small amount of material wherein the phytyl group has hydrolyzed; at 48 hours the tumor contains mainly material without phytyl and without Mg. At 24 hours the material in tumor is demetallized but still contains phytyl.

EXAMPLE 5

Light Penetration

Comparison was made using bchla at 20 mg/kg with irradiation after 1 hour at 270 $J/cm^2$ at 780 nm, and DHE at 5 mg/kg after 1 hour at 270 $J/cm^2$ at 630 nm. Animals with tumors approximately 1 cm in depth were used in the comparison. Histological sections were obtained the day following treatment, fixed and stained. A comparison using a total of 4 animals showed a necrotic depth of 5–6 mm for DHE and approximately 9 mm for bchla, consistent with deeper penetration of 780 nm light compared to 630 nm light.

I claim:

1. A method to effect the destruction or impairment of undesired target biological substrates, which method comprises:

a) treating said biological substrates with a compound of formula (1):

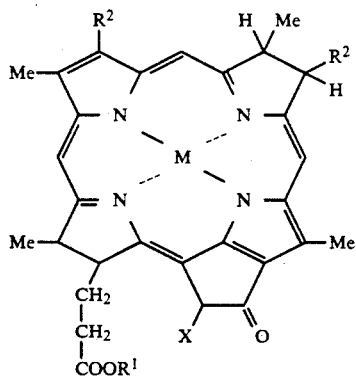 (1)

wherein

M is a non-paramagnetic metal selected from $Mg^{+2}$, $Sn^{+2}$, and $Zn^{+2}$, or represents $2H^{+}$ each H bonded to one of the N atoms connected by the solid lines;

$R^1$ is a saturated or unsaturated hydrocarbyl residue of 8–25C;

each $R^2$ is independently selected from the group consisting of vinyl, ethyl, acetyl and 1-hydroxyethyl, and X is $COOR^3$, wherein $R^3$ is alkyl (1–4C);

said compound of formula (1) being in an amount effective to photosensitize said biological substrates to the resultant of irradiation absorbed by the compound of formula (1); and (b) irradiating the treated biological substrates with radiation having a wavelength absorbed by the compound of formula (1).

2. The method of claim 1 wherein the target biological substrates are contained in the body of a mammalian subject and said treating is effected by systematically administering the compound of formula (1), or a pharmaceutical composition thereof, to said subject.

3. The method of claim 1 wherein the target biological substrates are contained on the skin of a mammalian subject and said treating is effected by topically administering the compound of formula (1), or a pharmaceutical composition thereof, to said subject.

4. The method of claim 1 wherein said biological substrates are contained in an in vitro biological fluid and said treating is conducted by adding the compound of formula (1) to the biological fluid.

5. The method of claim 4 wherein the biological fluid is blood or blood plasma.

6. The method of claim 1 wherein the target biological substrate is selected from the group consisting of tumor cells, bacterial cells, fungi, protozoa and viruses.

7. The method of claim 1 wherein $R^1$ is a phytyl residue and M is $Mg^{+2}$.

8. The method of claim 1 wherein one $R^2$ is acetyl and the other $R^2$ is vinyl or ethyl.

9. The method of claim 8 wherein the compound of formula (1) is bacteriochlorophyll-a or bacteriochlorophyll-b.

10. The method of claim 1 wherein the radiation is generated by a diode laser.